United States Patent
Lee et al.

(10) Patent No.: US 8,569,240 B2
(45) Date of Patent: Oct. 29, 2013

(54) METHODS OF PREVENTING OR TREATING BRAIN DISEASES

(75) Inventors: Heejae Lee, Chuncheon (KR); Jong-Seon Byun, Chuncheon (KR); Kyung Young Lee, Chuncheon (KR); Dahlkyun Oh, Chuncheon (KR)

(73) Assignee: Regeron, Inc., Chuncheon Ganwon-Do (KR)

( * ) Notice: Subject to any disclaimer, the term of this patent is extended or adjusted under 35 U.S.C. 154(b) by 0 days.

(21) Appl. No.: 13/209,437

(22) Filed: Aug. 14, 2011

(65) Prior Publication Data
US 2012/0040910 A1 Feb. 16, 2012

Related U.S. Application Data

(63) Continuation-in-part of application No. 12/843,690, filed on Jul. 26, 2010, which is a continuation-in-part of application No. PCT/KR2009/000364, filed on Jan. 23, 2009.

(30) Foreign Application Priority Data

Jan. 25, 2008 (KR) .................. 10-2009-0006151

(51) Int. Cl.
*A01N 37/18* (2006.01)
*A61K 38/00* (2006.01)

(52) U.S. Cl.
USPC .................. 514/17.7; 514/17.8; 514/21.3

(58) Field of Classification Search
None
See application file for complete search history.

(56) References Cited

U.S. PATENT DOCUMENTS

2004/0198658 A1 10/2004 Olsen et al.

FOREIGN PATENT DOCUMENTS

| WO | 00/16795 A1 | 3/2000 |
| WO | 2006/031843 A2 | 3/2006 |

OTHER PUBLICATIONS

Zhang, Ke-zhou et al., "Stanniocalcin: A molecular guard of neurons during cerebral ischemia": Neurobiology, PNAS, vol. 97, No. 7, p. 3637-3642; Mar. 28, 2000.
Conlong, J. Michael, "Singular contributions of fish neuroendocriniology to mammalian regulatory peptide research", Regulatory Peptides, Elsevier: Mar. 12, 2000.

*Primary Examiner* — Olga N Chernyshev
(74) *Attorney, Agent, or Firm* — Edwards Wildman Palmer LLP

(57) ABSTRACT

The present invention relates to methods for preventing or treating neurological diseases, particularly brain diseases, and improving cognitive functions using a composition comprising stanniocalcin 2 as an active ingredient.

10 Claims, 8 Drawing Sheets

Fig. 2
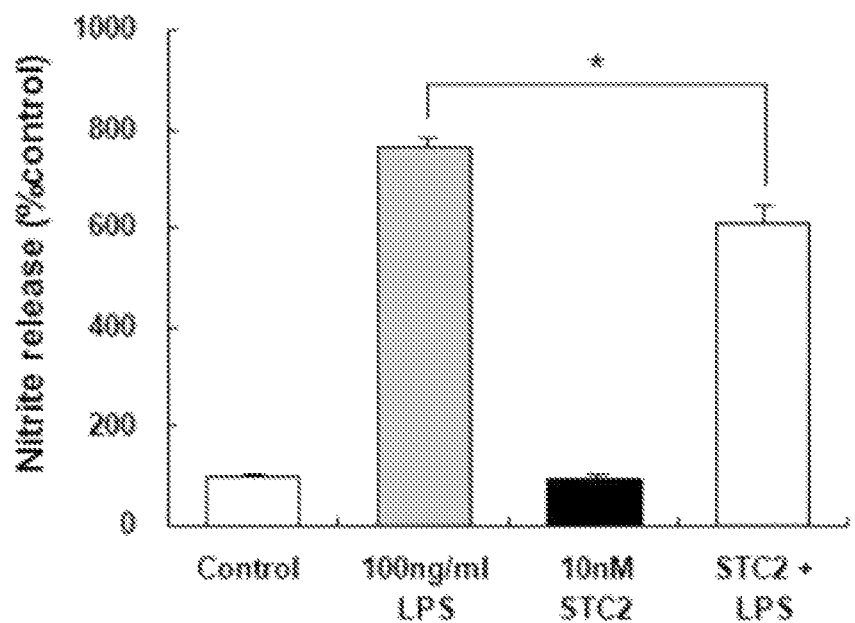
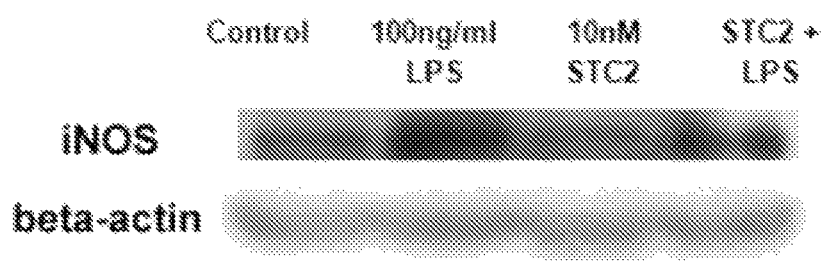

SEQUENCE LISTING

```
<160> NUMBER OF SEQ ID NOS: 13

<210> SEQ ID NO 1
<211> LENGTH: 279
<212> TYPE: PRT
<213> ORGANISM: Homo sapiens

<400> SEQUENCE: 1

Met Thr Asp Ala Thr Asn Pro Pro Glu Gly Pro Gln Asp Arg Ser Ser
1               5                   10                  15

Gln Gln Lys Gly Arg Leu Ser Leu Gln Asn Thr Ala Glu Ile Gln His
            20                  25                  30

Cys Leu Val Asn Ala Gly Asp Val Gly Cys Gly Val Phe Glu Cys Phe
        35                  40                  45

Glu Asn Asn Ser Cys Glu Ile Arg Gly Leu His Gly Ile Cys Met Thr
    50                  55                  60

Phe Leu His Asn Ala Gly Lys Phe Asp Ala Gln Gly Lys Ser Phe Ile
65                  70                  75                  80

Lys Asp Ala Leu Lys Cys Lys Ala His Ala Leu Arg His Arg Phe Gly
                85                  90                  95

Cys Ile Ser Arg Lys Cys Pro Ala Ile Arg Glu Met Val Ser Gln Leu
            100                 105                 110

Gln Arg Glu Cys Tyr Leu Lys His Asp Leu Cys Ala Ala Ala Gln Glu
        115                 120                 125

Asn Thr Arg Val Ile Val Glu Met Ile His Phe Lys Asp Leu Leu Leu
    130                 135                 140

His Glu Pro Tyr Val Asp Leu Val Asn Leu Leu Leu Thr Cys Gly Glu
145                 150                 155                 160

Glu Val Lys Glu Ala Ile Thr His Ser Val Gln Val Gln Cys Glu Gln
                165                 170                 175
```

```
Asn Trp Gly Ser Leu Cys Ser Ile Leu Ser Phe Cys Thr Ser Ala Ile
            180                 185                 190

Gln Lys Pro Pro Thr Ala Pro Pro Glu Arg Gln Pro Gln Val Asp Arg
        195                 200                 205

Thr Lys Leu Ser Arg Ala His His Gly Glu Ala Gly His His Leu Pro
    210                 215                 220

Glu Pro Ser Ser Arg Glu Thr Gly Arg Gly Ala Lys Gly Glu Arg Gly
225                 230                 235                 240

Ser Lys Ser His Pro Asn Ala His Ala Arg Gly Arg Val Gly Gly Leu
                245                 250                 255

Gly Ala Gln Gly Pro Ser Gly Ser Ser Glu Trp Glu Asp Glu Gln Ser
            260                 265                 270

Glu Tyr Ser Asp Ile Arg Arg
            275

<210> SEQ ID NO 2
<211> LENGTH: 840
<212> TYPE: DNA
<213> ORGANISM: Homo sapiens

<400> SEQUENCE: 2
atgaccgacg ccaccaaccc acccgagggt ccccaagaca ggagctccca gcagaaaggc      60
cgcctgtccc tgcagaatac agcggagatc cagcactgtt tggtcaacgc tggcgatgtg     120
gggtgtggcg tgtttgaatg tttcgagaac aactcttgtg agattcgggg cttacatggg     180
atttgcatga ctttttctgca caacgctgga aaatttgatg cccagggcaa gtcattcatc    240
aaagacgcct tgaaatgtaa ggcccacgct ctgcggcaca ggttcggctg cataagccgg     300
aagtgcccgg ccatcaggga atggtgtcc cagttgcagc gggaatgcta cctcaagcac      360
gacctgtgcg cggctgccca ggagaacacc cgggtgatag tggagatgat ccatttcaag     420
gacttgctgc tgcacgaacc ctacgtggac ctcgtgaact gctgctgac ctgtggggag      480 gaggtgaagg aggccatcac ccacagcgtg caggttcagt gtgagcagaa ctggggaagc     540
ctgtgctcca tcttgagctt ctgcacctcg gccatccaga agcctccac ggcgcccccc      600 gagcgccagc cccaggtgga cagaaccaag ctctccaggg cccaccacgg ggaagcagga     660
catcacctcc cagagcccag cagtaggag actggccgag gtgccaaggg tgagcgaggt     720
agcaagagcc acccaaacgc ccatgcccga ggcagagtcg ggggccttgg ggctcaggga     780
ccttccggaa gcagcgagtg gaagacgaa cagtctgagt attctgatat ccggaggtga      840

<210> SEQ ID NO 3
<211> LENGTH: 25
<212> TYPE: DNA
<213> ORGANISM: Homo sapiens

<400> SEQUENCE: 3
ccggaattca tgtgtgccga gcggc                                            25

<210> SEQ ID NO 4
<211> LENGTH: 29
<212> TYPE: DNA
<213> ORGANISM: Homo sapiens

<400> SEQUENCE: 4
ggatctccgc tgtattctgc agggacagg                                        29

<210> SEQ ID NO 5
```

```
<211> LENGTH: 28
<212> TYPE: DNA
<213> ORGANISM: Homo sapiens

<400> SEQUENCE: 5
cagaatacag cggagatcca gcactgtt                                              28

<210> SEQ ID NO 6
<211> LENGTH: 28
<212> TYPE: DNA
<213> ORGANISM: Homo sapiens

<400> SEQUENCE: 6
atgacttgcc ctgggcatca aattttcc                                              28

<210> SEQ ID NO 7
<211> LENGTH: 30
<212> TYPE: DNA
<213> ORGANISM: Homo sapiens

<400> SEQUENCE: 7
gatgcccagg gcaagtcatt catcaaagac                                            30

<210> SEQ ID NO 8
<211> LENGTH: 27
<212> TYPE: DNA
<213> ORGANISM: Homo sapiens

<400> SEQUENCE: 8
cacgtagggt tcgtgcagca gcaagtc                                               27

<210> SEQ ID NO 9
<211> LENGTH: 27
<212> TYPE: DNA
<213> ORGANISM: Homo sapiens

<400> SEQUENCE: 9
gctgcacgaa ccctacgtgg acctcgt                                               27

<210> SEQ ID NO 10
<211> LENGTH: 30
<212> TYPE: DNA
<213> ORGANISM: Homo sapiens

<400> SEQUENCE: 10
ggggtacctc acctccggat atcagaatac                                            30

<210> SEQ ID NO 11
<211> LENGTH: 34
<212> TYPE: DNA
<213> ORGANISM: Homo sapiens

<400> SEQUENCE: 11
gtatcagagg tgtctatgac cgacgccacc aacc                                       34

<210> SEQ ID NO 12
<211> LENGTH: 30
<212> TYPE: DNA
<213> ORGANISM: Homo sapiens

<400> SEQUENCE: 12
ccggaattcg taaacctctt ccttcaggct                                            30

<210> SEQ ID NO 13
```

-continued

```
<211> LENGTH: 26
<212> TYPE: DNA
<213> ORGANISM: Homo sapiens

<400> SEQUENCE: 13
catagacacc tctgatactc gtttcg                                              26
```

METHODS OF PREVENTING OR TREATING BRAIN DISEASES

CROSS-REFERENCE TO RELATED APPLICATIONS

This application is a continuation-in-part of U.S. patent application Ser. No. 12/843,690 filed on Jul. 26, 2010, which is a continuation-in-part of International Application PCT/KR2009/000364, filed on Jan. 23, 2009 and published as WO 2009/093864 on Jul. 30, 2009, which claims the benefit of Korean Application No. 10-2009-0006151 filed on Jan. 25, 2008 and published as KR 2009-0082154 on Jul. 29, 2009, the contents of which are incorporated herein by reference in their entireties.

BACKGROUND OF THE INVENTION

1. Field of the Invention

The present invention relates to methods for preventing and/or treating neuronal diseases, brain diseases in particular, and improving cognitive functions using a composition comprising STC2 as the active ingredient.

2. Description of the Related Art

Many biological factors and pathways are known to be involved with the onset of various neuronal diseases. Microglial activation in the central nervous system is one of such factors associated with critical neurodegenerative brain disorders.

Microglia are a type of glial cells that are resident macrophages of the brain and spinal cord, and thus act as the first and main form of active immune defense in the central nervous system (CNS). By undergoing a variety of structural changes based on their location and given roles, they have diversified functions which include constant excavation of the CNS for damaged neurons, destroying infectious organisms via phagocytosis, and secretion of anti-inflammatory cytokines. Without microglial cells CNS regrowth and remapping would be considerably slower. However, in the case of chronic neural inflammation (neuroinflammation) process or sustained injury, microglial cells produce neurodegenerative symptoms such as plaque formation, hence contribute to and expand the neurodestructive effects, worsening the disease process (Streita et al., Trends in Neurosciences, 2006, 29 (9): 506-510). In that, microglia release a variety of cytotoxic substances hence can injure neurons through NMDA receptor-mediated processes (Moriguchi et al., Brain Res Mol Brain Res, 2003, 119(2), 160-169). As a result, chronic inflammatory response can result in a large scale neural damage as the microglia ravage the brain in an attempt to destroy the invading infection (Gehrmann et al., Brain Research Reviews, 1995, 20 (3), 269-287).

Accordingly, evidence indicates that microglial activation is responsible for the occurrence of many neuronal disorders; 1) epilepsy and/or seizure (Wirenfeldt et al., Neurobiology of Disease, 2009, 34(3), 432-44; Taniwaki et al., Neuroscience Research, 1996, 24-26(20), S80), 2) Parkinson's disease (Long-Smith, et al. Prog Neurobiol. 2009, 89, 277-287), 3) Alzheimer and Parkinson's diseases (Laskowitz et al., Exp Neurol, 2001, 167, 74-85; Itagaki et al., Advances in Behavioral Biology, 1993, 38(A), 381). In addition, suppression of microglial activation has been shown to be linked to protection of neuronal cells (Li et al., J Neurosci Res 2001, 66, 163-170).

A disease model was developed that expresses the phenotypes resulting from downregulated neurogenesis and disclosed a composition that effectively treat and prevent neuronal disorders (US20110021435). In relation to that invention, we now disclose methods that can treat and prevent various neuronal deficits and/or malfunctions, especially in the brain, by suppressing the microglial activation and a composition comprising stanniocalcin 2 (STC2) as the active ingredient.

Stanniocalcin 2 is a functional homodimeric glycoprotein and generally recognized as a hormonal or other type of regulator like its widely studied paralog stanniocalcin 1 (STC1) (Luo et al., Endocrinology, 2005, 146(1), 469-476). Although STC1 and STC2 share some similarities, accumulating evidence indicates that they have different structures and functions. For instance, STC2 shares amino acid sequence identity to STC1 by less than 35% (Ishibashi et al., Biochemical and Biophysical Research Communications, 1998, 250 (2), 252-8; Ishibashi et al., Am J Physiol Renal Physiol. 2002, 282 (3): F367-75; Chang and Reddel, Molecular and Cellular Endocrinology, 1998, 141 (1/2):95-99)). Furthermore, Blast analysis results demonstrate that the nucleotide sequence of human STC2 has no hits with significant matching with those of STC1 regardless of its species or tissue origin. Most importantly, in contrast to STC1, the predicted amino acid sequence of STC2 contains a cluster of histidine residues in the C-terminal portion of the protein that STC1 is devoid of, implying additional functions in relation to metal binding (Chang and Reddel, Molecular and Cellular Endocrinology, 1998, 141(1/2), 95-99).

Both STC2 and STC1 are found in various tissues including neuronal cells (Shin et al., Comparative Biochemistry and Physiology. Part A, Molecular & Integrative Physiology, 2009, 153(1), 24-29). Earlier studies demonstrated distinct properties between the two as follows: 1) Serum Ca2+ and PO4 were unchanged in STC2-overexpressing transgenic mice, although STC-1 can regulate intra- and extracellular Ca2+ in mammals (Gagliardi et al., Am J Physiol Endocrinol Metab. 2005, 288(1):E92-105); 2) much higher level of STC2 expression during development (ibid.); 3) STC1 is phosphorylated by a different type of kinase from STC2 in fibrosarcoma cells (Jellinek et al., Biochemical Journal, 2000, 350(2), 453-461); 4) the function of STC2 seems opposite to that of STC1 on Na-phosphate cotransporter in that STC2 inhibited the phosphate uptake in a kidney cell line whereas STC1 stimulates the phosphate uptake of kidney (Ishibashi et al., Biochemical and Biophysical Research Communications, 1998, 250(2), 252-8); 5) opposite (i.e., increased vs. decreased) mRNA expression between STC1 and STC2 under a given condition (Honda et al., *FEBS Letters,* 1999, 459, 119-122; Jellinek et al., Endocr Relat Cancer, 2003, 10(3), 359-73); 6) distinct processes regulate STC1 and STC2 secretion from the same cell, possibly reflecting different biological roles (Jellinek et al., Biochemical Journal, 2000, 350(2), 453-461). In spite of these distinct differences, both STC1 and STC2 act as a potent growth inhibitor and reduce intramembranous and endochondral bone development and skeletal muscle growth (Gagliardi et al., Am J Physiol Endocrinol Metab. 2005, 288(1), E92-105). For STC2, such growth-suppressive properties of human stanniocalcin-2 in transgenic mice were shown to be exerted independently from growth hormone and IGFs (ibid).

It has been disclosed that a high level of constitutive contents of STC1 in mammalian brain neurons (Serlachius et al., Peptides, 2004 25(10), 1657-62), and the expression of STC1 being related to terminal differentiation of neural cells (ibid; Koide et al., Rinsho Byori, 2006, 54(3), 213-20). STC2 and STC1 share dissimilarities and similarities in neural cell activities: 1) Both STC2 and STC1 were suggested to be pro-survival factors for the endurance of terminally differentiated cells such as neurons and adipocytes (Joensuu et al., Cancer Letters, 2008, 265(1), 76-83); 2) STC1 expression was upregulated by hypoxia in a manner different from that for STC2 (Ito et al., Molecular and Cellular Biology, 2004, 24(21), 9456-69); 3) STC2 expression was activated in neuronal cells by oxidative stress and hypoxia via mechanisms involving UPR (unfolded protein response), but not by several other cellular stresses unrelated to the UPR (ibid); 4) A cDNA microarray study demonstrated that STC2 gene was upregulated by responding to β-amyloid in human neuroblastoma cells (Kim et al., Experimental & Molecular Medicine, 2003, 35(5), 403-411) as stanniocalcin-1 (STC1) was upregulated by β-amyloid treatment in a time and dose-dependent manner in human brain microvascular endothelial cells (Li et al., Biochemical and Biophysical Research Communications, 2008, 376(2), 399-403)

SUMMARY OF THE INVENTION

Brain damage induced by microglial activation is demonstrated in the present invention by treating animals with kainic acid (KA), which was used to assess and prove the effectiveness of STC2 in protecting against neuronal damage.

The present invention relates to the surprising discovery that administration of STC2 to damaged brain regions substantially suppressed the microglial activation induced by KA in an animal model. Therefore, this invention relates to methods for preventing and treating neurological disorders, brain diseases in particular, and improving cognitive functions using a composition comprising STC2 as the active ingredient by suppressing the microglial activation.

Thus, it is one object of this invention to provide a method for preventing or treating a brain disease using a composition comprising stanniocalcin 2 as an active ingredient.

It is another object of this invention to provide a method for improving a cognitive function using a composition comprising stanniocalcin 2 as an active ingredient.

BRIEF DESCRIPTION OF THE DRAWINGS/FIGURES

FIG. 1. Immunoreactivity of OX-6 in the hippocampus of KA-injected ICR mice co-administered with STC2. Resting type of microglia was observed in the saline-treated group (FIGS. 1A, 1D). After KA treatment, microglia were activated (FIGS. 1B, 1D), but not in the KA and STC2 co-treated group (FIGS. 1C, 1F). The arrow indicates CA3 region. Scale bar 100 um.

FIG. 2. STC2 attenuates LPS-stimulated nitrite release (FIG. 2A) and iNOS expression (FIG. 2B) in BV2 microglial cells. In the presence of LPS (100 ng/ml), nitrite and iNOS expression were significantly induced in BV2 microglial cells, whereas pretreatment of 10 nM STC2 significantly reduced LPS-induced release of nitrite and iNOS expression. Data represent three independent experiments and were expressed as mean±S.D.*P<0.05 indicates statistically significance.

DETAILED DESCRIPTION OF THE INVENTION

Technical Problems to be Solved

Figure 1:
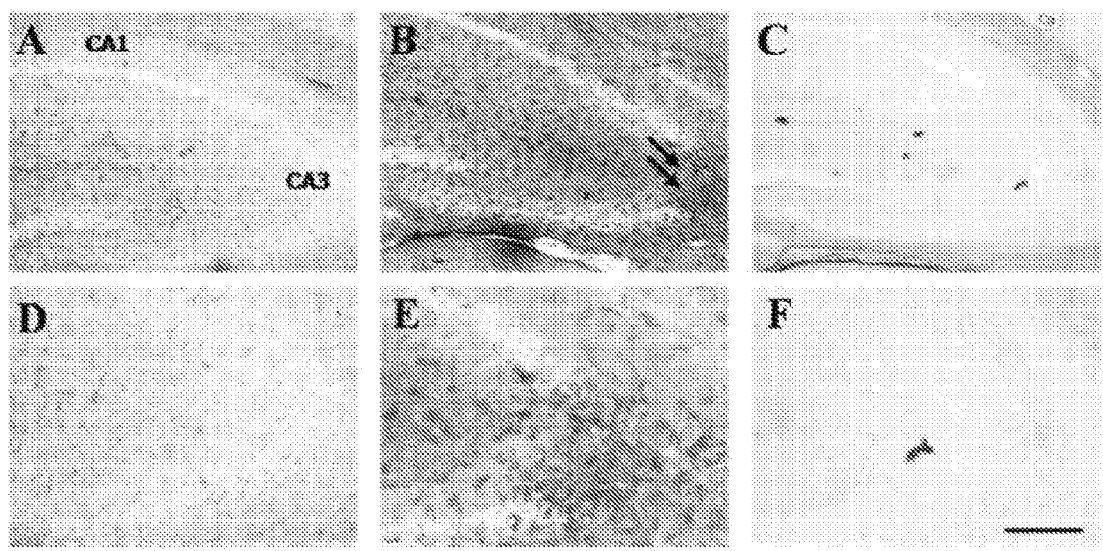

The present invention attempts to treat and prevent targeted neuronal disorders using STC2, which are caused by neuronal toxicity, such as seizures/epilepsy, Parkinson's disease, Huntington's disease, Parkinson's disease and amyotrophic lateral sclerosis (ALS) and/or to improve cognitive functions, e.g., treating Alzheimer's disease, but not the neurological disorders originated from hypoxic stress, such as cerebral infarction, ischemia, stroke or injuries due to attack or thromboembolism, or calcium mediated diseases.

Technical Solutions for Overcoming Technical Problems

The present invention relates to the important role played by microglial activation in damaging neuronal cells, especially in brain diseases and the ability of STC2 to prevent or treat the brain damage. Administration of STC2 to animals with hippocampus region affected with significant microglial activation substantially suppresses the activation, hence reduces or prevents the brain damage.

This invention relates to methods using a composition comprising STC2 as the active ingredient for preventing and treating neurological disorders, brain diseases in particular, and improving cognitive functions by suppressing the microglial activation.

Therefore, one aspect of this invention is to provide a method for preventing or treating a brain disease through the suppression of microglial activation using a composition comprising STC2 as the active ingredient.

Another aspect of this invention is to provide a method for improving a cognitive function through the suppression of microglial activation using a composition comprising STC2 as the active ingredient.

Thus far, the utility of STC2, its biologically functional derivatives, and the fragments has been demonstrated in the diagnosis and treatment of type II diabetes and chronic conditions associated with diabetes according to the claims made in WO0108697. Although the use of STC1 had been disclosed for treating neuronal diseases or protecting damaged neuronal cells (WO0130969 and the families, US20020042372 and US20040198658), it should be emphasized that in these prior arts, the neuroprotective functions of STC1 have been mainly implicated for disorders related to hypoxic stress, such as cerebral infarction, ischemia, stroke or injuries due to attack or thromboembolism, or calcium mediated diseases, but not for the treatment of seizures/epilepsy, Parkinson's disease, or improving cognitive functions which are the target disorders that this invention attempts to treat and prevent using STC2.

In another embodiment, this invention provides a disease model that expresses the phenotype resulting from microglial activation in order to assess and prove the efficacy of STC2 in treatment of various neuronal disorders. Since the neurological diseases described above in the Related Arts section involve toxicity incurred in neurons, the use of excitatory amino acids (kainic acid, NMDA, glutamate, etc.) allows the creation of non-human in-vivo models representing disorders due to microglial activation and disorder of brain functions.

Kainic acid (KA), in particular, is chosen for generating a disease model in the present invention due to its well established capability for inducing microglial activation (Taniwaki et al., Neuroscience Research, 1996, 24-26(20), S80). KA injection causes reactive gliosis and induces extensive microglial activation (Lee et al., J Pineal Res, 2006, 40, 79-85; Sperk et al., Neuroscience 1983, 10, 1301-15). The treatment of animals with KA resulted in in-vivo models with neuronal diseases, such as epilepsy, seizures (Urino et al., Neurologia Medico-Chirurgica, 2010, 50(5), 355-360), Parkinson's disease (Foster et al., Pteridines and Folates, Chemistry and Biology of Pteridines and Folates, 2002, 393-398), Alzheimer's disease (Mohmmad et al., J Neurochemistry, 2006, 96(5), 1322-35), and Cognitive Dysfunction (Srivastava et al., Neurochemical Research, 2008, 33(7), 1169-77). Interestingly, treatment of non-human subjects with kainic acid was shown to depress hypoxic effects (Sinclair J D, Respiration Physiology, 1990, 80(1), 55-70).

It is from this perspective that we have treated animals with KA directly at the hippocampus region, which is the area where neuronal cells are actively reproduced and responsible for learning and memory function via reciprocal electrical stimulation. Thus brain diseases due to downregulated neurogenesis and/or microglial activation are associated with this region. Stannicalcin 2 was applied to the affected region of hippocampus, i.e. with activated microglia, to prove its efficacy for treating the disorders.

In another embodiment, this invention assesses and proves the effects of STC2 in suppressing microglial activation in vitro using BV2 cell culture treated with lipopolysaccharide (LPS), besides its impact in in vivo (mouse) model.

The term "prevention" used herein refers to inhibiting the generation of disorders or diseases in animal who are not diagnosed as having but are susceptible to such disorders or diseases. As used herein, the term "treatment" refers to (a) inhibiting the development of disorders or diseases; or (b) ameliorating or (c) removing the disorders or diseases.

The term "stanniocalcin 2" used herein refers to human stanniocalcin 2 unless otherwise indicated. The amino acid sequence of human STC2 (279 amino acid including N-terminal Met) is reproduced below:

(SEQ ID NO: 1)

```
M T D A T N P P E G P Q D R S S Q Q K G R L S L Q N T A E I Q H C L V N

A G D V G C G V F E C F E N N S C E I R G L H G I C M T F L H N A G K F

D A Q G K S F I K D A L K C K A H A L R H F G C I S R K C P A I R E M V

S Q L Q R E C Y L K H D L C A A A Q E N T R V I V E M I H F K D L L L H E

P Y V D L V N L L L T C G E E V K E A I T H S V Q V Q C E Q N W G S L C

S I L S F C T S A I Q K P P T A P P E R Q P Q V D R T K L S R A H H G E A

G H H L P E P S S R E T G R G A K G E R G S K S H P N A H A R G R V G G

L G A Q G P S G S S E W E D E Q S E Y S D I R R Stop.
```

The nucleotide sequence of a human STC2, which was used in the invention, is reproduced below (840 bp including start and stop codons):

(SEQ ID NO: 2)

```
atgaccgacgccaccaacccacccgagggtccccaagacaggagctcccagcagaaaggccgcctgt ccctgcagaatacagcggagatccagcactgtttggtcaacgctggcgatgtggggtgtggcgtgtttg aatgtttcgagaacaactcttgtgagattcggggcttacatgggatttgcatgacttttctgcacaacgct ggaaaatttgatgcccagggcaagtcattcatcaaagacgccttgaaatgtaaggcccacgctctgcg gcacaggttcggctgcataagccggaagtgcccggccatcagggaaatggtgtcccagttgcagcgg gaatgctacctcaagcacgacctgtgcgcggctgcccaggagaacacccgggtgatagtggagatga tccatttcaaggacttgctgctgcacgaaccctacgtggacctcgtgaacttgctgctgacctgtgggga ggaggtgaaggaggccatcacccacagcgtgcaggttcagtgtgagcagaactggggaagcctgtg ctccatcttgagcttctgcacctcggccatccagaagcctcccacggcgcccccgagcgccagcccca ggtggacagaaccaagctctccagggcccaccacggggaagcaggacatcacctcccagagcccag cagtagggagactggccgaggtgccaagggtgagcgaggtagcaagagccacccaaacgcccatg cccgaggcagagtcgggggccttggggctcagggaccttccggaagcagcgagtgggaagacgaac agtctgagtattctgatatccggaggtga
```

The composition used for this invention is a pharmaceutical composition or a food composition: The pharmaceutical composition of this invention includes (a) a therapeutically effective amount of stanniocalcin 2; and (b) a pharmaceutically acceptable carrier In the pharmaceutical compositions used in this invention, the pharmaceutically acceptable carrier may be conventional one for formulation, including carbohydrates (e.g., lactose, amylase, dextrose, sucrose, sorbitol, mannitol, starch, cellulose), acacia rubber, calcium phosphate, alginate, gelatin, calcium silicate, fine crystallite cellulose, polyvinylpyrrolidone, cellulose, water, syrups, salt solution, alcohol, Arabian rubber, vegetable oil (e.g., corn oil, cotton seed oil, soybean oil, olive oil and coconut oil), poly(ethylene glycol), methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative, but not limited to. Details of suitable pharmaceutically acceptable carriers and formulations can be found in *Remington's Pharmaceutical Sciences* (19th ed., 1995), which is incorporated herein by reference.

The pharmaceutical composition used the present invention may be administered via orally or parenterally. When the pharmaceutical composition of the present invention is administered parenterally, it can be done by intravenous, subcutaneous, intramuscular and intracerebroventricular administration.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians with average skill may easily determine and diagnose dosage level of medicine effective for treating or preventing target disorders or diseases. Preferably, the pharmaceutical composition of the present invention is administered with a daily dose of 0.0001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The composition of the present invention may be provided as a food composition, particularly a functional food composition. The functional food composition of the present invention may be formulated in a wide variety of forms, for example, including proteins, carbohydrates, fatty acids, nutrients, seasoning agents and flavoring agents. As described above, an example of carbohydrate may include monosaccharides (e. g., glucose, fructose, etc.); disaccharides (e. g., maltose, sucrose, etc.); oligosaccharides; polysaccharides (e. g., common sugars including dextrin, cyclodextrin, etc.); and sugar alcohols (e. g., xylitol, sorbitol, erythritol, etc.). The formulation of flavoring agent may use natural flavoring agents (e. g., thaumatin, stevia extract (e.g., rebaudioside A, glycyrrhizin), etc.) and synthetic flavoring agents (e. g., saccharine, aspartame, etc.). In the formulation of drinking agent, it may further include citric acid, liquid fructose, sweet, glucose, acetic acid, malic acid, fruit syrup, eucommia bark extract, jujube extract and glycyrrhiza extract. Considering easy accessibility of food, the food composition herein is very useful in prevention or treatment of brain disorders or diseases, or improvement of cognitive function.

The present invention offers benefits and technical advantages by providing methods using a composition comprising stanniocalcin 2 as an active ingredient for preventing or treating critical neuronal diseases, particularly brain diseases, and for improving cognitive functions by suppressing the microglial activation.

The following Examples are intended to provide for those skilled in the art more concrete illustration of the effectiveness and relevant procedures as well as the scope of the present invention as set forth in the appended claims, which are not limited to by the examples.

EXAMPLES

1. Effects of STC2 on Microglial Activation

Kainic acid (KA) induces microglial activation and subsequent iNOS expression in the region of neuronal cell death (Byun et al., Korean J Physiol Pharmacol, 2009, 13, 265-71). In the present study, 5 μl of mixture solution (containing 0.1 μg kainic acid and 100 ng hSTC2 in 5 μl solution) was intracerebroventricularly (I.C.V) injected to male ICR mouse with weight of 23-25 g. All mice were sacrificed at 24 h after KA injection and were transcardially perfused with 50 mM PBS, then with chilled 4% paraformaldehyde in phosphate buffer (pH 7.4). The brains were cryoprotected in 30% sucrose, sectioned coronally (40 μm) on a freezing microtome, and collected in cryoprotectant. For cresyl violet staining, the sections were mounted on gelatin-coated slides and air-dried. The mounted sections were soaked in a cresyl violet solution. The results show that KA induced microglial activation, particularly in the CA3 region of the hippocampus (FIGS. 1B and 1E). However, co-treatment with STC2 markedly attenuated KA-induced microglial activation (FIGS. 1C and 1F). According to the present invention STC2 plays a protective role in excessive neurotoxicity.

2. Effects of STC2 on Lipopolysaccharide (LPS)-Induced NO Production and iNOS Expression in BV2 Cells The BV2 immortalized murine microglial cell line obtained from T. H. Joh (Burke Institute, Cornell University, USA) were cultured in Dulbecco's modified Eagle's medium (DMEM; Gibco BRL, Grand Island, N.Y., USA) supplemented with 10% fetal bovine serum (FBS; Gibco BRL) and penicillinstreptomycin (Gibco BRL). Cells were maintained in a humidified incubator at 37° C. with 5% CO2. The cell cultures were treated with 200 ng/ml of LPS. Cells were subcultured when they were grown to about 90% of bottom area, and cells of exponential growth phase were used for further experiments. To assess the ability of STC2 to regulate nitric oxide release stimulated by LPS, we exposed BV2 cells to STC2 for 2 h, followed by exposure to 200 ng/ml LPS for an additional 20 h. LPS significantly increased NO release and iNOS expression in BV2 cells, and pretreatment with STC2 significantly reduced the LPS-induced NO release and iNOS expression (FIG. 2). STC2 treatment alone did not significantly after nitric oxide release from BV2 cells (FIG. 2A).

3. Drug Treatment

To inhibit microglia activity, cells were treated with hSTC2 at a final concentration of 10 nM. As a microglia activator, LPS (lipopolysaccharide) was added at a final concentration of 200 ng/ml.

4. Immunohistochemistry

Five μl of KA (0.1 μg/5 μl, Tocoris), or 5 μl of mixture solution (containing 0.1 μg KA and 100 ng hSTC2 in 5 μl solution) was intracerebroventricularly (I.C.V) injected to four-week-old male mouse with weight of 23-25 g. After injection for 24 hrs, experimental animals were subjected to perfusion fixation using 4% paraformaldehyde preperfusion solution. Afterward, brain was immediately extracted from the animals and was washed with 30% sucrose solution for 24 hrs after postfixation in equal solution for 4 hrs. The brain tissues were frozen using OCT compounds. Tissue sections with 40 μm thickness was prepared using a freezing microtome and added with cryoprotectant solution, followed by being stored at −20° C. for immunohistochemistry. In first experimental day, brain tissues immersed in cryoprotectant solution were washed three times with 50 mM PB for 5 min. The tissues was treated with 3% $H_2O_2$ (in 50 mM PB) for 10 min to remove endogenous peroxidase, and incubated with 50 mM PB, 1% BSA and 0.2% Triton X-100 for 30 min. After incubating with 50 mM PB, 0.5% BSA and 3% normal serum for 1 hr, the tissues were washed with 50 mM PB for 10 min, and immunohistochemically stained with using anti-OX-42 monoclonal antibody. Next day, the brain tissues were washed three times with 50 mM PB for 5 min, and incubated with goat anti-mouse IgG secondary antibody (1:200) contained in 50 mM PB and 0.5% BSA for 1 hr, followed by washing three times with 50 mM PB for 5 min. The tissues were incubated with ABC reagent (1:200) for 1 hr, and washed three times with 50 mM PB for 5 min, followed by colorimetric reaction using DAB as a substrate. After stopping reaction, the tissues had transparent by dehydration using conventional methods and finally embedded in polymount.

5. Measurement of Nitric Oxide (NO) Concentration

The production of nitric oxide (NO) was determined by measuring concentration of nitrite ($NO_2^-$). using colorimetric assay with Griess reagent (1% sulfanilamide, 0.1% naphthylethylenediamine dihydrochloride/2.5% $H_3PO_4$).

6. Mouse Y-Maze Test

Figure 3:
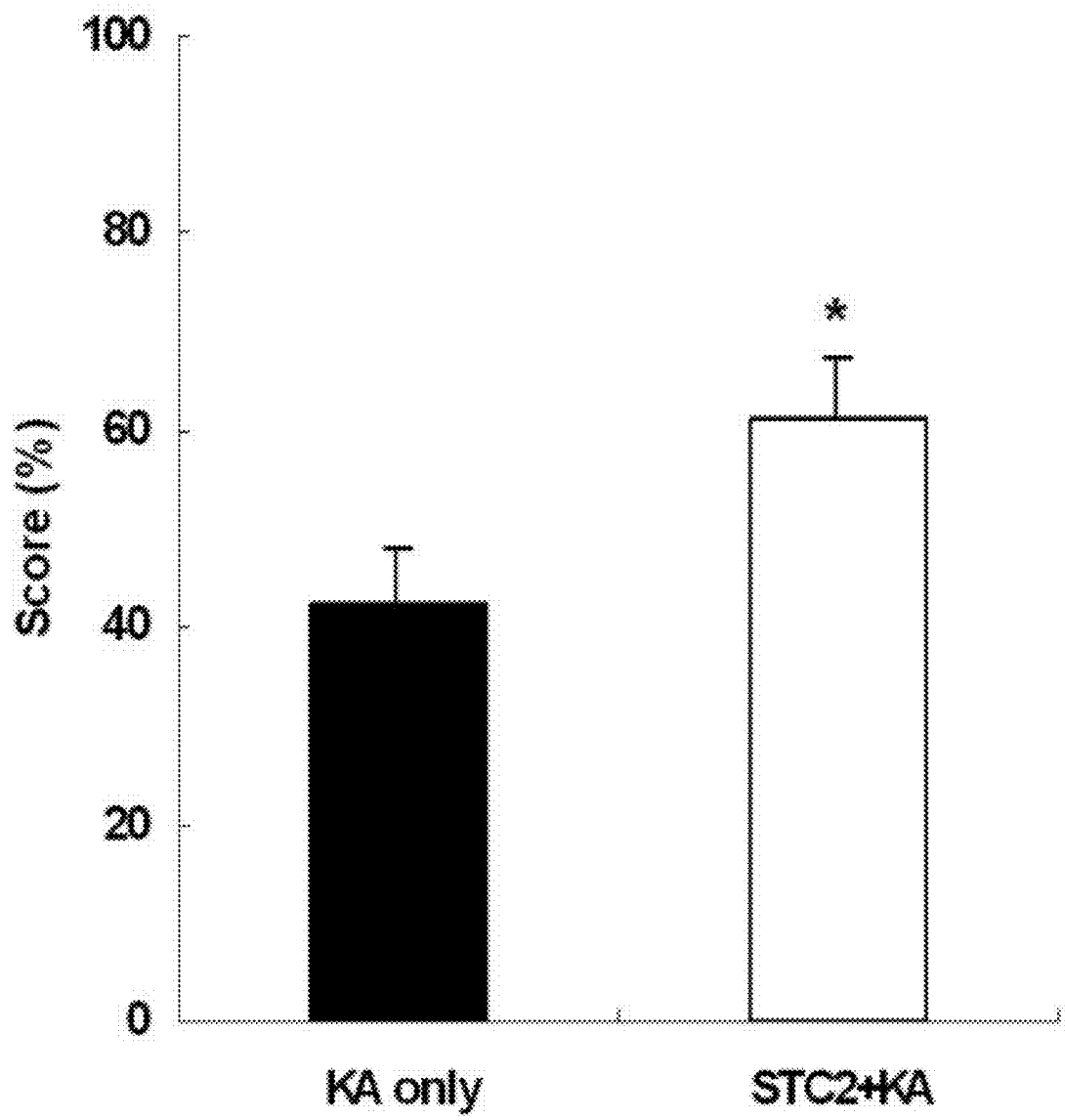
FIG. 3 represents Y-maze behavior in mouse, demonstrating that the score of place memory in hSTC2-treated group is significantly increased compared to KA alone-treated group (p<0.05).

Four-week-old male ICR mouse (DBL, Korea) with weight of 23-25 g was randomly divided into two groups (control and test), and each group consists of five mice. Five μl of kainic acid (0.1 μg/5 μl, Tocoris) and 5 μl of mixture solution (containing 0.1 μg kainic acid and 100 ng hSTC2 in 5 μl solution) were intracerebroventricularly (I.C.V) injected to control and test group, respectively. After injection for 24 hrs, Y-maze experiment was performed to examine cognitive function. Y-maze device is composed of three arms with 40 (width)×12 (length)×30 (height), and experiment was carried out in intensity of illumination of 20±5 lux. Each three arms consisting of Y-maze was randomly named as A, B and C. After a head part of mouse was put toward the passage in the end of an arm, mouse wandered into the passage in a free manner for 8 min to observe movement path. Passing of the arm on Y-maze of this invention means that hind legs of mouse are entered into the passage of an arm. As described above, arms that mouse passes were sequentially recorded and then tied up three in a sequence. As a result, it was considered as one point that all paths (arms) is independently different, which mouse passes. For example, where mouse passes the arm in a sequence of ABCAC, the order of ABC, BCA and CAC is tied, giving two points. Memory score (%) is calculated as follows: total score is divided by (total path number-2) and converted to percentage. The present experiment is carried out to examine place memory function using research and curiosity which are basic characteristics in rodents. Memory score was 42.5±5.4% in KA (kainic acid) alone-treated group and 61.3±6.3% in the group treated with both hSTC2 and KA, suggesting that memory score decreased by KA is remarkably enhanced by hSTC2 (FIG. 3).

7. Mouse Water Finding Test

Figure 4:
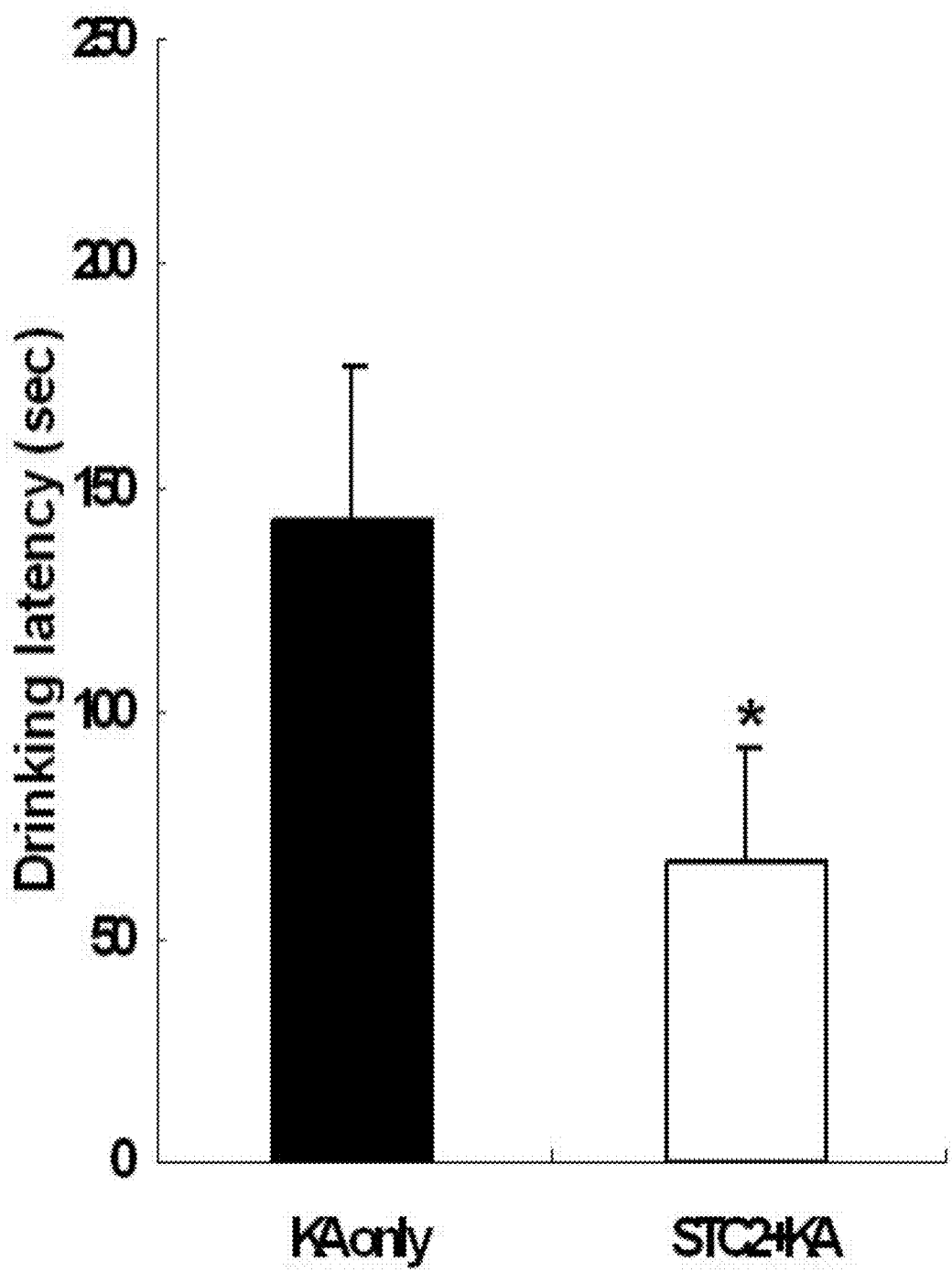
FIG. 4 is a water finding test in mouse and drinking latency in hSTC2-treated group is significantly reduced compared to KA alone-treated group, meaning excellent learning memory (p<0.05).

Four-week-old male ICR mouse (DBL, Korea) with weight of 23-25 g was randomly divided into two groups (control and test), and each group consists of five mice. Five μl of kainic acid (0.1 μg/5 μl, Tocoris) and 5 μl of mixture solution (containing 0.1 μg kainic acid and 100 ng hSTC2 in 5 μl solution) were intracerebroventricularly (I.C.V) injected to control and test group, respectively. After injection for 24 hrs, water finding test was performed to suppose latent learning. A device was a box in a size of 30 (width)×50 (length)×20 (height), and its bottom was divided into 15 spaces of 10×10 cm, of which a door of 10×10 cm was prepared one wall, and a water bottle was put inside the door. In first day, mouse injected with kainic acid alone or kainic acid and STC2 was placed in one end of the space and learned to drink water. After learning, the supply of water was stopped for 24 hrs. In second day, the mouse was again put into the device, and then the time (sec) of drinking latency was measured. The present experiment is carried out to estimate learning, place memory and working memory. In high level of learning and memory function, drinking latency is relatively short. Drinking latency in hSTC2-treated group (67±25 sec) is significantly decreased compared to that in KA alone-treated group (143±34 sec) (p<0.05) (FIG. 4).

8. Mouse Forced Swim Test

Figure 5:
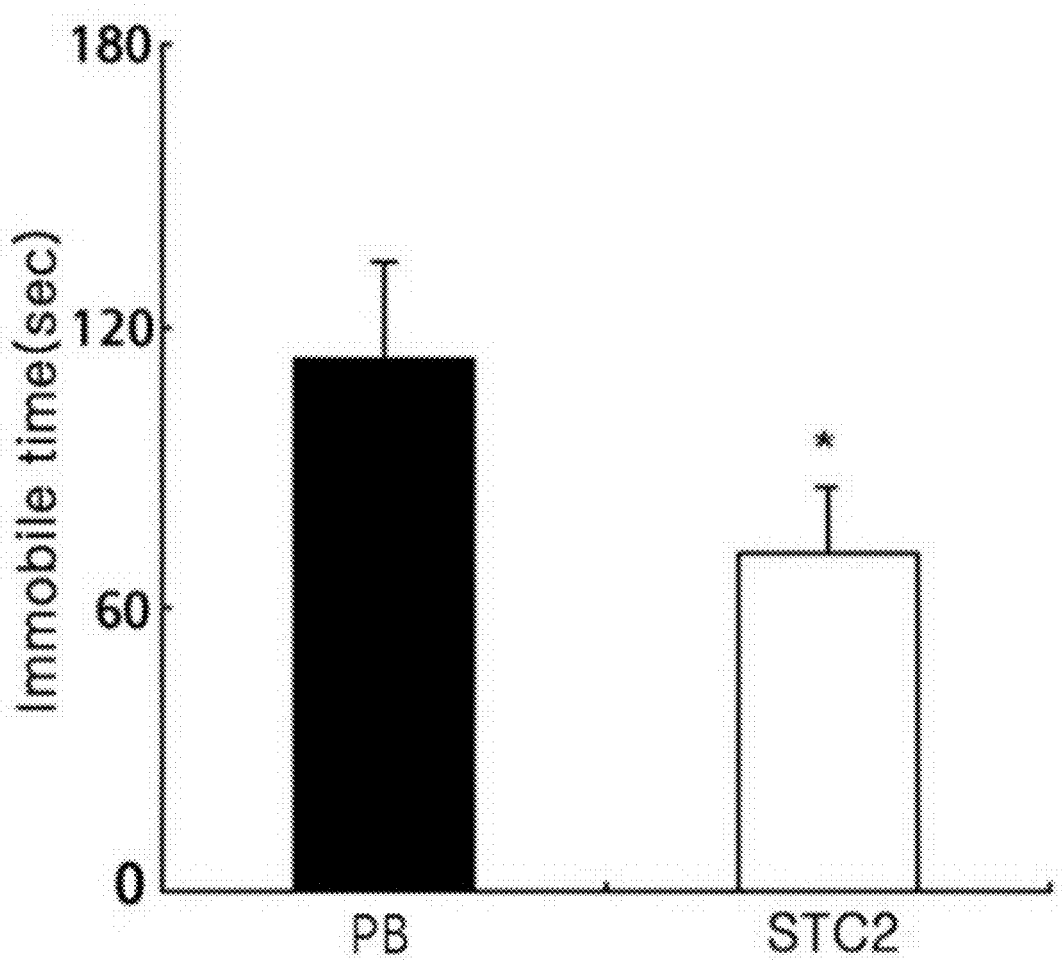
FIG. 5 is a forced swim test in mouse and immobile time in hSTC2-treated group is significantly reduced compared to PB-treated group, representing effective efficacy on improvement of depression-related behavior (p<0.05).

Four-week-old male ICR mouse (DBL, Korea) with weight of 23-25 g was randomly divided into two groups (control and test), and each group consists of five mice. Five μl of PBS and 5 μl of hSTC2 (100 ng/5 μl) were intracerebroventricularly (I.C.V) injected to control and test group, respectively. After injection for 24 hrs, immobilization stress was forced for 2 hrs. After stress, the mouse was subjected to forced swim for 6 min in circular water bath (diameter, 10 cm; height, 20 cm) containing water of 25±2° C. Two min later, the time in an immobile floating posture that the face of mouse is floated on the surface of the water was measured for 4 min. An immobile behavior is known to be helplessness. The present test is commonly utilized as a depression animal model for observation and assessment of depression-related behavior. The longer immobile time criterion, the higher helplessness estimated from the test. Immobile time in hSTC2-treated group (71±15 sec) is significantly reduced compared to that in a KA alone-treated group (113±21 sec) (p<0.05) (FIG. 5).

9. Stanniocalcin 2 (STC2) Preparation

Genomic DNA was extracted from HEF (Human embryonic fibroblast) and used as template after cutting with BamHI (Takara, Japan). PCR was carried out to obtain four DNA fragments for exon encoding stanniocalcin 2. To ligate exon DNA fragments, primers were designed for base pairing between 19 bases in a linking region, and PrimeSTAR™ HS DNA polymerase (Takara, Japan) was used in all PCR reactions. To amplify exon 1, 2, 3 and 4 of stanniocalcin 2, the first PCR method is as follows: (a) genomic DNA cut with BamHI (Takara, Japan) was commonly used as a template; and (b) PCR cycle (98° C. 10 sec; 55° C. 5 sec; and 72° C. 30 sec) using hSTC2 1U primer (Bioneer, Korea) and hSTC2 2D primer, obtaining 169 by exon 1 fragment. According to the method as described above, 163 by exon 2, 231 by exon 3, and 420 exon 4 were obtained using hSTC2 3U primer and hSTC2 4D primer, hSTC2 5U primer and hSTC2 6D primer, and hSTC2 7U primer and hSTC2 8D primer, respectively.

Second PCR utilized exon 1 (169 bp), exon 2 (163 bp), exon 3 (231 bp) and exon 4 (420 bp) obtained by the above-described method as a template, and PCR using hSTC2 1U containing EcoRI (Takara, Japan) restriction site (GAATTC) and hSTC2 8D containing KpnI restriction site (GGTACC) was carried out for 30 cycles of 98° C. 10 sec; 55° C. 5 min; and 72° C. 1 min to obtain 926 by stanniocalcin 2.

The resulting DNA encoding stanniocalcin 2 and pUC-18 (Amersham Pharmacia Biotech, Swiss) was restricted with EcoRI and KpnI (Takara, Japan), and ligated with T4 DNA ligase (Takara, Japan), followed by transformation into Top10F' E. coli. After incubating at 37° C. for 15 hrs, three colonies randomly selected were cultured and plasmids were obtained according to alkaline lysis method. These plasmids were electrophoresized on 1% agarose gel and then desirable plasmid (pUC-hSTC2) was selected by analysis using nucleotide sequence kit (Solgent, Korea).

PCR was carried out to link Met-stanniocalcin 2 in which narK promoter and signal sequence are removed, and primers were designed for base pairing between 18 bases in a linking region. The first PCR method is as follows: (a) pNKmut plasmid (−10 mutated narK promoter; Regeron Inc.) was commonly used as a template; and (b) PCR cycle (98° C. 10 sec; 55° C. 5 sec; and 72° C. 25 sec) using OY-17 and r-narK D primer pair, obtaining 350 by narK promoter. PCR (30 cycles: 98° C. 10 sec; 55° C. 5 sec; and 72° C. 55 sec) was carried out using pUC-hSTC2 as a template and hSTC2 9U and hSTC2 8D primer pair to obtain 863 by Met-stanniocalcin 2.

Second PCR utilized narK promoter (350 bp) and Met-stanniocalcin 2 (420 bp) obtained by the above-described method as a template, and PCR using OY-17 containing EcoRI (Takara, Japan) restriction site (GAATTC) and hSTC2 8D containing KpnI restriction site (GGTACC) was carried out for 30 cycles of 98° C. 10 sec; 55° C. 5 min; and 72° C. 1 min to obtain 1,195 by fragments containing Met-stanniocalcin 2 which narK promoter and signal sequence is removed. 1,195 by fragments (containing Met-stanniocalcin 2 which narK promoter and signal sequence is removed) and pUC-rrnB (rrnB terminator is inserted into pUC18; Regeron Inc.) were restricted with EcoRI and KpnI, and ligated with T4 DNA ligase, followed by transformation into Top10F' E. coli. After incubating at 37° C. for 15 hrs, three colonies randomly selected were cultured and plasmids were obtained according to alkaline lysis method. These plasmids were electrophoresized on 1% agarose gel and then desirable plasmid (pUC-narK Met-hSTC2) was selected by analysis using nucleotide sequence kit.

Figure 6:
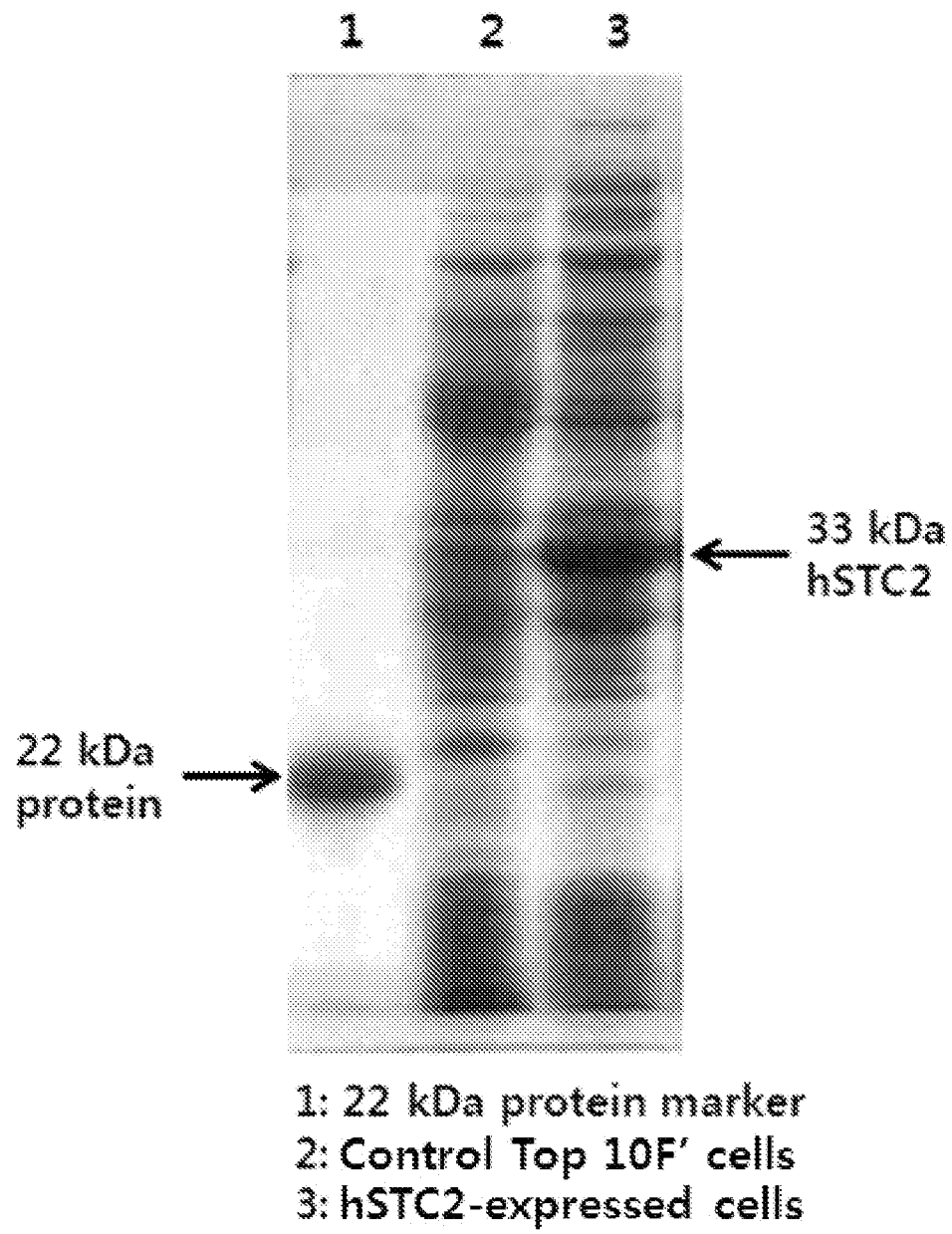
FIG. 6 is SDS-PAGE of purified hSTC2, indicating 33 kDa band of purified hSTC2.

Ten g of Top10F' cells transformed with pUC-narK Met-hSTC2 was suspended in 200 ml of 50 mM EDTA solution, and then sonicated, followed by centrifuging at 10,000 g for 30 min to collect precipitates. The precipitates were resuspended and then analyzed on SDS-PAGE. As shown in FIG. 6, about 33 kDa band indicating hSTC2 was observed. In addition, 33 kDa band on SDS-PAGE was eluted and incubated with trypsin (Promega, US) at 37° C. for 16 hrs. As a result, it could be demonstrated that the band is hSTC2 using MALDI-TOF (Applied Biosystems, US) and MS-Fit search (Protein Prospector).

The centrifuged precipitates were mixed to 200 ml distilled water, and 1 ml of 100% Triton X-100 was added to a concentration of 0.5%, followed by shaking at room temperature for 30 min. The precipitates were harvested by centrifuging at 10,000 g for 30 min. The precipitates were dissolved in 200 ml distilled water, and stirred at room temperature for 30 min. The precipitates were collected by centrifuging at 10,000 g for 30 min. After the precipitates were mixed with solution A (50 mM Tris pH 8.0, 6 M Urea, 10 mM 2-Mercaptoethanol), the mixture was stirred at room temperature for 90 min, and centrifuged at 10,000 g for 40 min, obtaining the supernatant.

Figure 7:
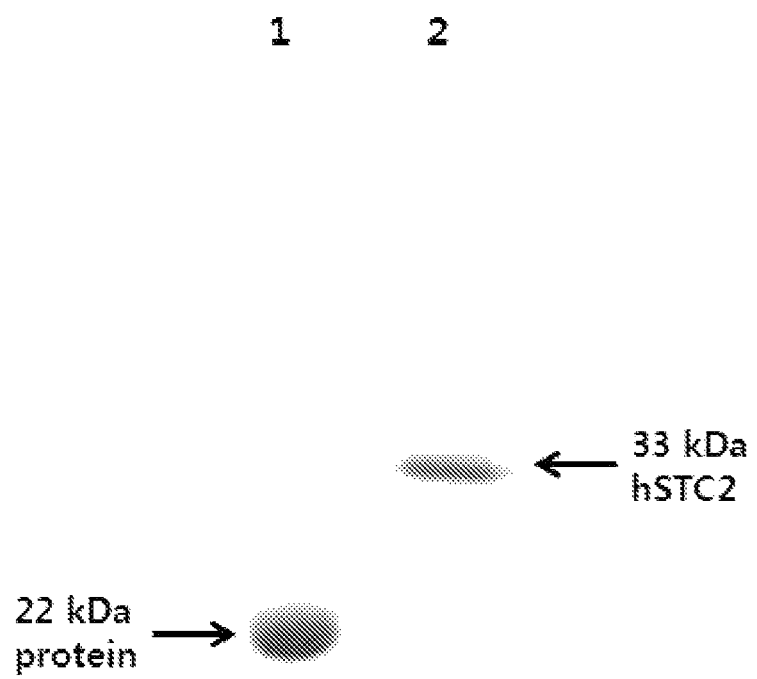
FIG. 7 is SDS-PAGE of purified hSTC2, indicating 33 kDa band of purified hSTC2. Lane 1 is protein size marker; and lane 2 is purified hSTC2.
Figure 8:
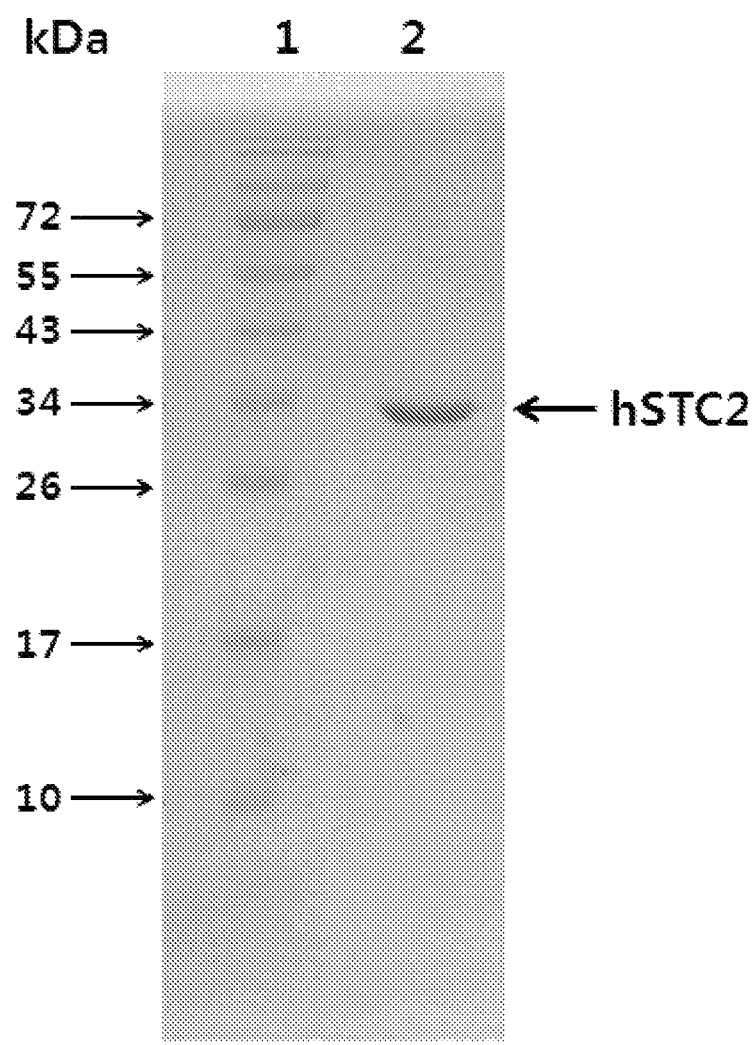
FIG. 8 represents Y-maze behavior in mouse, demonstrating that the score of place memory in hSTC2-treated group is significantly increased compared to KA alone-treated group (p<0.05).

The supernatant was diluted with 200 ml distilled water, and adsorbed to gel by passing DEAE-Sepharose column (GE Healthcare) pre-equilibrated with a buffer solution (20 mM Tris, 1 mM EDTA), followed by washing with the buffer solution (20 mM Tris, 1 mM EDTA). The adsorbed proteins were eluted from the gel using a buffer solution (20 mM Tris, 1 mM EDTA, 300 mM NaCl). The eluent is subjected to gel filtration chromatography using Superdex 200 (GE Healthcare) pre-equilibrated with a buffer solution (20 mM $NaH_2PO_4$, 1 mM EDTA, pH 7.0). The eluted fractions were electrophoresized on 15% SDS-PAGE (FIG. 7) to collect only the fractions which hSTC2 purity is higher than 90%. Finally, purified hSTC2 (not less than 90% purity; FIG. 8) was measured at 595 nm using Bradford assay with standard protein (BSA; bovine serum albumin) and Spectra MAX 190 (Molecular Device Inc.), obtaining quantitative protein amount of 0.125 mg/ml. Final purified hSTC2 was utilized in further experiments.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES CITED

The following documents are cited herein.
U.S. Patent Documents
US20110021435
US20020042372
US20040198658

TABLE

Primer nucleotide sequences.

| Primer | Nucelotide sequence (5'→3') |
|---|---|
| hSTC2 1U | CCGGAATTCATGTGTGCCGAGCGGC (25 mer) |
| hSTC2 2D | GGATCTCCGCTGTATTCTGCAGGGACAGG (29 mer) |
| hSTC2 3U | CAGAATACAGCGGAGATCCAGCACTGTT (28 mer) |
| hSTC2 4D | ATGACTTGCCCTGGGCATCAAATTTTCC (28 mer) |
| hSTC2 5U | GATGCCCAGGGCAAGTCATTCATCAAAGAC (30 mer) |
| hSTC2 6D | CACGTAGGGTTCGTGCAGCAGCAAGTC (27 mer) |
| hSTC2 7U | GCTGCACGAACCCTACGTGGACCTCGT (27 mer) |
| hSTC2 8D | GGGGTACCTCACCTCCGGATATCAGAATAC (30 mer) |
| hSTC2 9U | GTATCAGAGGTGTCTATGACCGACGCCACCAACC (34 mer) |
| OY-17 | CCGGAATTCGTAAACCTCTTCCTTCAGGCT (30 mer) |
| r-narK D | CATAGACACCTCTGATACTCGTTTCG (26 mer)] |

(Table sequences are SEQ ID NOs: 3-13, respectively)

Foreign Patent Documents
WO0108697
WO0130969
KR20090082154

OTHER REFERENCES

Byun et al., Korean J Physiol Pharmacol, 2009, 13, 265-71.
Chang and Reddel, Molecular and Cellular Endocrinology, 1998, 141 (1/2), 95-99.
Foster et al., Pteridines and Folates, Chemistry and Biology of Pteridines and Folates, 2002, 393-398.
Gagliardi et al., Am J Physiol Endocrinol Metab. 2005, 288 (1):E92-105.
Gehrmann et al., Brain Research Reviews, 1995, 20 (3), 269-287.
Honda et al., FEBS Letters, 1999, 459, 119-122.
Ishibashi et al., Am J Physiol Renal Physiol. 2002, 282 (3), F367-75.
Ishibashi et al., Biochemical and Biophysical Research Communications, 1998, 250 (2), 252-8.
Itagaki et al., Advances in Behavioral Biology, 1993, 38(A), 381.
Ito et al., Molecular and Cellular Biology, 2004, 24(21), 9456-69.
Jellinek et al., Biochemical Journal, 2000, 350(2), 453-461.
Jellinek et al., Endocr Relat Cancer, 2003, 10(3), 359-73.
Joensuu et al., Cancer Letters, 2008, 265(1), 76-83.
Kim et al., Experimental & Molecular Medicine, 2003, 35(5), 403-411.
Koide et al., Rinsho Byori, 2006, 54(3), 213-20.
Laskowitz et al., Exp Neurol, 2001, 167, 74-85.
Lee et al., J Pineal Res, 2006, 40, 79-85.
Li et al., Biochemical and Biophysical Research Communications, 2008, 376(2), 399-403.
Li, et al., J Neurosci Res, 2001, 66, 163-170.
Long-Smith, et al., Prog Neurobiol, 2009, 89, 277-287.
Luo et al., Endocrinology, 2005, 146(1), 469-476.
Moriguchi et al., Brain Res Mol Brain Res, 2003, 119(2), 160-169.
Mohmmad et al., J Neurochemistry, 2006, 96(5), 1322-35.
Serlachius et al., Peptides, 2004 25(10), 1657-62.
Shin et al., Comparative Biochemistry and Physiology. Part A, Molecular & Integrative Physiology, 2009, 153 (1), 24-29.
Sinclair J D, Respiration Physiology, 1990, 80(1), 55-70.
Sperk et al., Neuroscience 1983, 10, 1301-15.
Srivastava et al., Neurochemical Research, 2008, 33(7), 1169-77.
Streita et al., Trends in Neurosciences, 2006, 29 (9), 506-510.
Taniwaki et al., Neuroscience Research, 1996, 24-26(20), S80.
Urino et al., Neurologia Medico-Chirurgica, 2010, 50(5), 355-360.
Wirenfeldt et al., Neurobiology of Disease, 2009, 34(3), 432-44.

What is claimed is:

1. A method for improving a cognitive function of a subject, the method comprising administering to a subject a therapeutically acceptable amount of a composition comprising as an active ingredient stanniocalcin 2 having an amino acid sequence of SEQ ID NO:1.

2. The method according to claim 1, wherein the subject suffers from a neurodegenerative disease.

3. The method according to claim 1, wherein the composition is administered orally or parenterally.

4. The method according to claim 2, wherein the composition is administered orally or parenterally.

5. The method according to claim 1, wherein the cognitive function is learning ability, memory or concentration.

6. A method for improving a cognitive function of a subject, the method comprising administering to the subject a therapeutically acceptable amount of a composition comprising as an active ingredient stanniocalcin 2 having an amino acid sequence encoded by a nucleotide sequence of SEQ ID NO:2.

7. The method of claim 6, wherein the subject suffers from a neurodegenerative disease.

8. The method according to claim 6, wherein the composition is administered orally or parenterally.

9. The method according to claim 7, wherein the composition is administered orally or parenterally.

10. The method according to claim 6, wherein the cognitive function is learning ability, memory or concentration.

* * * * *